United States Patent [19]

Dolhyj et al.

[11] 4,336,198

[45] Jun. 22, 1982

[54] PREPARATION OF MALEIC ANHYDRIDE USING COATED CATALYSTS CONTAINING HIGH LOADING OF ACTIVE PHASE

[75] Inventors: Serge R. Dolhyj, Parma; Marc A. Pepera, Broadview Heights, both of Ohio

[73] Assignee: The Standard Oil Company, Cleveland, Ohio

[21] Appl. No.: 271,153

[22] Filed: Jun. 8, 1981

Related U.S. Application Data

[62] Division of Ser. No. 104,603, Dec. 17, 1979, Pat. No. 4,312,787.

[51] Int. Cl.$^3$ ............................................. C07D 307/60
[52] U.S. Cl. ..................................... 549/259; 549/260
[58] Field of Search ..................................... 260/346.75

[56] References Cited

U.S. PATENT DOCUMENTS 4,077,912  3/1978  Dolhyj et al. ..................... 252/461
4,097,501  6/1978  Dolhyj et al. ................. 252/437 X Primary Examiner—Henry R. Jiles
Assistant Examiner—Bernard Dentz
Attorney, Agent, or Firm—Joseph G. Curatolo; Herbert D. Knudsen; Larry W. Evans

[57] ABSTRACT

Catalysts particularly effective in the oxidation of n-butane, n-butenes, 1,3 butadiene and mixtures thereof with molecular oxygen or an oxygen-containing gas in the vapor phase to produce maleic anhydride are provided which comprise an essentially inert, at least partially porous support to which is adhered on its outer surface, catalytically active mixed oxides of vanadium and phosphorus or of vanadium, phosphorus and uranium in an amount greater than 50% to about 80% by weight of the combined support and active oxide.

17 Claims, No Drawings

PREPARATION OF MALEIC ANHYDRIDE USING COATED CATALYSTS CONTAINING HIGH LOADING OF ACTIVE PHASE

This is a division of application Ser. No. 104,603 filed Dec. 17, 1979 now U.S. Pat. No. 4,312,787 issued Jan. 26, 1982.

BACKGROUND OF THE INVENTION

Catalysts containing vanadium and phosphorus oxides have been used in the oxidation of 4-carbon atom hydrocarbons, such as n-butane, n-butenes, 1,3 butadiene or mixtures thereof with molecular oxygen or oxygen-containing gas to produce maleic anhydride.

Representative vanadium-phosphorus catalysts and methods of their preparation are disclosed in U.S. Pat. Nos. 4,043,943 and 4,132,670 and vanadium-phosphorus-uranium catalysts and methods of their preparation are disclosed in U.S. Pat. Nos. 4,002,650 and 4,172,084, the latter two patents being assigned to our common Assignee of record herein. These catalysts may be utilized in either fluid bed or fixed bed reactors for the production of maleic anhydride. Before the catalytic material can be utilized, however, it must be converted from its post-preparation form, usually a dry powder, to a form suitable to be charged to a commerical reactor.

A catalytic powder is conventionally compressed into the form of pellets or tablets for use in commercial reactors. This procedure is costly, time consuming, and rather difficult as it requires subjecting the powder to high pressures, exemplified by European Patent Application No. 3,431 as being on the order of 16 tons per sq. in. to 27 tons per sq. in.

When pellets are utilized, the catalytic material on the interior of the pellet often does not participate in the reaction, because the reactant often cannot diffuse far enough into the interior of the pellet for the catalytic material which is present there to affect the reactants. Because this high cost catalytic material does not participate in the reaction, it is essentially wasted.

One alternate method of forming catalytic material so that it can be utilized in a commercial reactor is the coating of the catalytic material on a support or carrier, as described in U.S. Pat. No. 4,077,912, owned by our common Assignee. A coating method was utilized with catalysts useful in preparing maleic anhydride from benzene as described in U.S. Pat. No. 4,097,501, also owned by our common assignee. These patents disclose that the reactions thus catalyzed are most favorably effected when the amount of the active catalyst material is present as a coating on a support or carrier in the amount of about 10–100% by weight of the support, that is, in the amount of about 5–50% of the combined weight of catalytic oxide material and support.

Catalysts for the oxidation of 4-carbon atom hydrocarbons such as butane do not, however, give acceptable yields when present as a coating in these proportions. When the catalytic oxide material is present in an amount less than 50% of the combined weight of the catalytic oxide material and support, the yield of the maleic anhydride from 4-carbon atom hydrocarbon feedstock is generally lower than would be achieved if the catalyst were in pelleted form.

U.S. Pat. No. 4,071,539 discloses catalysts consisting of oxides of vanadium, phosphorus, copper, and cerium, and oxides of vanadium, phosphorus, copper, tellurium, cerium and an alkali metal or an alkaline earth, useful in the preparation of maleic anhydride from 4-carbon hydrocarbons, which catalysts may be coated as a catalyst precursor solution, or as a catalyst precursor paste onto carriers and thereafter dried and calcined. In order to achieve yields of maleic anhydride with coated catalysts comparable to yields achieved with non-coated catalysts, the amount of catalytic material in these coatings was required to be in the range of about 85 to 92.5% of the combined weight of the carrier and catalytic material. The advantage of partially filling the reactor space with low cost carrier rather than high cost active material, while achieving the same or better yield, is lost when the amount of carrier material used is relatively insignificant, that is, when the amount of carrier is less than about 20% of the combined weight of the carrier and catalytic material.

SUMMARY OF THE INVENTION

Thus it is an object of the present invention to provide catalysts for the preparation of maleic anhydride from 4-carbon atom hydrocarbon feeds such as n-butane, n-butenes, 1,3 butadiene or mixtures thereof.

It is a further object of the present invention to provide catalysts for the preparation of maleic anhydride in a form suitable for use in commercial reactors, whether fluid bed or fixed bed reactors.

It is a further object of the present invention to provide catalysts for the preparation of maleic anhydride which can be easily produced and can be produced at low cost.

It is a further object of the invention to provide catalysts for the preparation of maleic anhydride from 4-carbon atom hydrocarbon feeds which catalysts comprise an inert support and a catalytically active oxide material strongly adhering to the surface of the support, in an amount which provides yields of maleic anhydride as good as or better than yields achieved by utilizing the catalytically active oxide material in pelleted form.

These and other objects, together with the advantages thereof over known methods, which shall become apparent from the specification which follows, are accomplished by the invention as hereinafter described and claimed. In general, catalysts of the present invention comprise an essentially inert, at least partially porous support to which is adhered on its outer surface, catalytically active mixed oxides of vanadium and phosphorus, or of vanadium, phosphorus and uranium in an amount greater than 50% to about 80% of the combined weight of the support and active oxide material.

In general, one method for preparing catalysts of the present invention includes the steps of wetting the carrier surface with a liquid by contacting the carrier, or support, with a liquid such that at least some liquid is absorbed by the support, contacting the partially wet support with a powder of the catalytically active oxide material to form a mixture and agitating the mixture of the wet support and catalytically active oxide material to form the coated catalyst. To obtain a high loading of active material on the support, it is preferable to include the further steps of wetting the catalytically active material-coated support, contacting the same with a further portion of a powder of the catalytically active oxide material and agitating the mixture, repeating the steps until the desired weight percent of catalytically active oxide material is achieved.

DETAILED DESCRIPTION OF THE INVENTION

The oxidation of 4-carbon atom hydrocarbons such as n-butane, n-butenes, 1,3 butadiene or a mixture thereof using catalysts consisting essentially of oxides of vanadium and phosphorus or of vanadium, phosphorus and uranium have been found to produce high yields of maleic anhydride. The conventional commercial form of these catalysts have been pellets having a high crush strength. It has been discovered that yields as high as or higher than those yields conventionally obtained with pelleted catalysts, can be obtained with catalysts comprising catalytically active oxide material and an inert support wherein the catalytically active oxide material is coated upon the inert support, in an amount greater than 50% to about 80% and preferably in an amount in the range of about 55% to about 70%, of the combined weight of the support and catalytically active material.

The essentially inert support may be selected from a wide choice of materials available in the art. This support material must have a diameter of at least about 20 microns. Preferred supports have a diameter of about 0.06 centimeters to about 1.3 centimeters, but there is no upper limitation on the size of the support material other than that dictated by the size of the reactor in which the catalyst is to be utilized.

The support material must be at least partially porous. By this is meant the support material must be susceptible to the penetration of liquid. Preferred support materials are capable of absorbing at least about 1% and more preferably 5% by weight of water based upon the weight of the support. The catalyst may have any shape, such as spheres, rings or irregular shapes which provide a higher surface area per unit weight of support. However, the present invention can be utilized to minimize reactor pressure drop by the use of spherical catalysts. These spherical catalysts are prepared by using a spherical support material and distributing the active catalytic material evenly on the outer surface of the support.

The inert support may be any material that is not active in the oxidation reaction. Suitable examples of essentially inert support materials include: Alundum, silica, alumina, alumina-silica, silicon carbide, titania and zirconia. Especially preferred among these supports are: Alundum, silica, alumina and alumina-silica.

The second component of the catalysts of the present invention is the catalytically active oxide material. The catalytically active oxides disclosed herein are not novel in themselves to the present invention, and may be prepared by known techniques. The catalytically active material consists essentially of the mixed oxides of vanadium and phosphorus, wherein P/V ratio is 0.1:1 to 10:1 and is preferably in the range of 0.5:1 to 3:1.

A second catalytically active material utilized in the present invention may be described by the empirical formula:

$$V_aP_bU_cO_x$$

wherein
a and b are 0.1 to 10;
c is 0.01 to 5; and
x is the number of oxygens required to satisfy the valence requirements of the other elements present.
Catalysts of special interest within this formula are described when a and b are 0.5 to 3, and c is 0.1 to 0.5.

The amount of catalytically active oxide material contained in the catalysts of the present invention is within the range of greater than 50% to about 80% by weight of the combined support and catalytically active material. Preferred catalysts contain catalytically active material in an amount of about 55% to about 70% by weight of the combined support and catalytically active material. The catalysts may include inert oxide support materials.

The preparation of these catalysts can be accomplished by various techniques. The basic method of preparing these catalysts is to partially wet the support material with a liquid. The support should not be wet on the outside surface of the total mass, but preferably should be dry to the touch. If the support is too wet, the active catalytic material will agglomerate into separate aggregates when coating of the support is attempted. These partially wet supports are then contacted with a powder of the catalytically active material with or without oxide support material and the mixture is gently agitated until the catalyst is formed.

Gentle agitation is most conveniently conducted by placing the partially wet support in a rotating drum and adding the active catalytic material until none is taken up by the support. If a greater loading, that is a more extensive coating, of the support is desired, the partially coated support may again be partially wet with a liquid, and this partially wet, partially coated support is then contacted with a further portion of a powder of the catalytically active material, and the mixture again gently agitated until the catalytic material is taken up by the support. This step may be repeated until the desired loading is achieved.

The liquid used to wet the support may include any inorganic or organic liquids which would not deleteriously effect the catalytically active material, such as water, alcohols, acids, ethers, ketones, aldehydes, and the like. Water is the preferred liquid.

SPECIFIC EMBODIMENTS OF THE INVENTION

Example 1

Catalytically active oxide material represented by the empirical formula $V_{1.0}P_{1.2}U_{0.2}O_x$ where x is the number of oxygens needed to satisfy the valence requirements of the other elements, was prepared according to the following procedure.

Two solutions were prepared as follows. Solution A was formed by placing 136.4 grams of $V_2O_5$ and 127.2 grams of uranyl acetate in a two liter flask, adding 750 ml of isobutanol and stirring the resultant slurry. Gaseous anhydrous HCl was added to the suspension with cooling being effected through aid of an ice bath. The HCl addition was carried out until total solubility was attained after an addition time of $2\frac{1}{4}$ hours. Solution B was formed by placing 207.5 g of 85% $H_3PO_4$ and 316 ml of isobutanol in a 1 liter flask. Water was removed by azeotropic distillation during the course of approximately 7 hours, 29 ml of water being recovered.

When the HCl addition of solution A was completed, the ice bath was removed, solution B was added to solution A and the mixture was heated to reflux. Reflux was continued for 90 minutes. The solution was then evaporated in a pot furnace at 150° C. for about 16 hours. The resulting solid was crushed and ground to pass through 50 mesh (0.297 mm) screen, 3% graphite being added.

A 30 wt.% coating of this active powder (based upon the combined weight of active powder and support) was effective upon an inert support, consisting of Norton SA 5209 ⅛ (0.31 cm) Alundum spheres by the following method.

Fifty grams of the support was wetted with 4.0 grams of distilled water by rolling in a glass jar. After 10 minutes the material was free flowing and had dry appearing surfaces. To this material, in a rotating jar, was added 21.43 grams of the catalytically active oxide powder in 5 equal incremental additions. After each addition, the resulting mixture was rolled for about 10 minutes. After the third addition and rolling, the material was sprayed with an additional about 2 grams of distilled water and rolled again. The addition of the fourth increment of powder with about 10 minutes of rolling was then performed and the addition of water, rolling, and addition of powder with rolling was repeated for the fifth incremental portion. The coated catalyst was then dried at 110° C. for about 16 hours, and was calcined in air in a muffle furnace at 400° C. for 16 hours.

Examples 2–3

A catalyst having the formula 50% $V_{1.0}P_{1.2}U_{0.2}O_x$+50% Alundum was prepared by coating of the inert support material described in Example 1 with the catalytically active oxide powder prepared in Example 1, but containing no graphite.

Fifty grams of Norton SA 5209 ⅛ inch (0.31 cm) was sprayed with 5.0 grams distilled $H_2O$, and rolled for 10 min. in a glass jar, at which time the material was free flowing and had a dry appearing surface. To this material was added 50 grams of catalytically active oxide powder in 5 incremental portions. The first two portions were added and rolled for 10 min. each. Additional spraying was required after the second addition and rolling steps. About 4 grams of distilled water was sprayed with about 10 min. of rolling, and a third portion of active powder was added. This required rolling for about 15 min. until all the active powder was taken up by the support. The spraying and rolling steps were repeated after the third and fourth incremental additions. The fourth incremental addition required about 30 min. of rolling, and the fifth incremental addition required about 40 min. rolling time until all the powder was taken up by the support. The evenly coated particles were dried at about 110° C. for about 16 hours and were calcined at 400° C. in a muffle furnace for about 16 hours.

Examples 4–5

Catalyst of the formula 70% $V_{1.0}P_{1.2}U_{0.2}O_x$+30% Alundum were prepared using catalytically active oxide material prepared as in Example 1 (containing no graphite) and inert support material described in Example 1. 30 grams inert support was placed in a rolling glass jar and sprayed with about 6 grams distilled water. This material was rolled for about 9 minutes. Seventy grams active powder was added to this material in five incremental portions. After each addition of powder, the mixture was rolled for times of about three minutes initially, increasing to about nine minutes for subsequent additions. After each addition of powder and rolling, an additional 1 gram of distilled water was sprayed onto the coated support with three minutes rolling. The coated catalysts were air dryed at room temperature for two hrs., with drying being completed by heating at 110° C. for about 16 hrs. The catalysts were calcined for at least 1 hour at 400° C.

Examples 6–8

Catalytically active oxide material having the empirical formula $V_{1.0}P_{1.2}U_{0.2}O_x$ was prepared as described in Example 1, except that an equivalent portion of $U_3O_8$ was substituted for the uranyl acetate and an equivalent portion of 100% orthophosphoric acid was substituted for the 85% orthophosphoric acid, avoiding the need for azeotropic distillation. No graphite was mixed with this material.

Catalysts having the formula 55% $V_{1.0}P_{1.2}U_{0.2}O_x$+45% Alundum were prepared using the catalytically active oxide powder prepared as described above and the inert support material described in Example 1.

409 grams of Norton Alundum SA 5209 ⅛" (0.31 cm.) spheres were charged to a large glass bottle of about 9 inches length (22.9 cm.) and 5¼ inches (13.3 cm.) diameter, on a Norton rolling mill at 50 revolutions per 27 sec. for a contact linear velocity of 76.8 cm. per second. 41 grams of distilled water was sprayed onto the Alundum support, which was rolled for five minutes. 500 grams active powder was charged to the rolling jar according to the following procedure. 100 grams active powder was added to the partially wet support and the mixture was rolled for about ten minutes. An additional 5.4 grams distilled water was sprayed and the mixture was rolled for an additional four minutes. A second 100 gram amount of active powder was added to the mixture and this was rolled for five minutes. About 36.6 grams of distilled water was added in seven approximately equal increments by spraying, with about three minutes of rolling after each addition.

A 50 gram increment of active powder was then charged to the mixture, and rolled for three minutes. Ten grams distilled water was added by spraying in two equal increments, with rolling for about three min. after each addition. This step was repeated with a second 50 gram increment of active powder. Two additional 50 gram increments of active powder were then added with three to six minute rolling times, and an additional 15 grams distilled water was sprayed in at least three increments followed by rolling for about three minutes for each 50 gram addition of active powder.

Fifty grams active powder was then added with three minutes rolling followed by two successive additions of five grams distilled water by spraying with three minutes rolling. A final 50 gram portion of active powder was added with three minutes rolling followed by spraying with 20 grams of distilled water in at least six increments, with a rolling time of about three minutes between each addition. The total material involved was 500 grams active powder, 409 grams Alundum and 163 grams distilled water. The coated catalyst had an apparent bulk density of about 1.044 grams per cubic centimeter before drying. The average outer diameter of the catalysts was about five millimeters, for a coating thickness of about 0.5 millimeters of active material. The catalysts were dried and calcined as in the proceeding examples.

Examples 9–14

Catalysts having the formula $V_{1.0}P_{1.2}U_{0.2}O_x$ were prepared according to the procedure in Example 1. For Examples 9, 10 and 11, the catalytically active oxide material was pelletized and calcined at 400° C. for 16 hrs. In Examples 12, 13 and 14, the catalytically active powder was tabletted and calcined as above.

The catalysts prepared in Example 1-14 were used to produce maleic anhydride from butane in a 40 cc fixed-bed reactor. The reactor was a stainless steel tube having an outer diameter of 1.91 cm. and an inner diameter of about 1.42 cm. and a length of about 30.5 cm. The reactor was heated with a split stainless steel block furnace. Flasks for receiving the product maleic anhydride were mounted in ice water, and tail gases were routed to a Carle Analytical Gas Chromatograph III for analysis. Reactor conditions are listed in Table I along with test results. The results are stated in terms as follows:

$$\text{Single Pass Yield} = \frac{\text{Moles of Maleic Anhydride Formed}}{\text{Moles of Butane Fed}} \times 100$$

$$\text{Total Conversion} = \frac{\text{Moles of Butane Reacted} \times 100}{\text{Moles of Butane Fed}}$$

$$\text{Selectivity} = \frac{\text{Single Pass Yield} \times 100}{\text{Total Conversion}}$$

As can be seen from the results listed in Table I, catalysts containing the mixed oxides of vanadium, phosphorus and uranium wherein the catalytic material is present as a coating on an inert support, effect a yield and selectivity of butane to maleic anhydride generally lower than the yields and selectivities effected by those catalysts in pelleted or tabletted form (100 wt.%), when the amount of catalytically active material is less than or equal to 50 wt.% of the combined catalytically active oxide material and support. When those catalysts are present in a coating upon an inert support in an amount greater than 50%, or in a preferred range of 55% to 70% of the weight of the combined catalytically active oxide material and support, the yields and selectivities of butane to maleic anhydride are generally improved as compared to the yields and selectivities exhibited by those catalysts in pelleted or tabletted form.

Example 15

Catalytically active oxide material having the empirical formula $V_{1.0}P_{1.16}O_x$ was prepared according to the following procedure. 800 grams of $V_2O_5$ was ball milled in 900 ml isobutanol for 1¾ hrs. This suspension was diluted to a total of seven liters with isobutanol, was stirred and refluxed for about 20 hours. This slurry was filtered through glass frits, removing unreacted $V_2O_5$. Based upon the weight of unreacted $V_2O_5$, it was determined that 160 grams had reacted and remained in solution. 200 grams of 100% orthophosphoric acid was dissolved in 600 ml isobutanol. The solutions were combined and heated under reflux for about 16 hours. The resulting precipitate was filtered out of solution, washed with isobutanol and was dried at 150° C. for two hours. A portion of the resulting powder was pelleted and then cracked, in order to be charged to a 20 cc fixed-bed reactor. Calcining was from 200° C. to 400° C. at a rate of 5°/minute with heating at 400° C. for one hour.

Examples 16-19

Catalysts were prepared having the formula 55% $V_{1.0}P_{1.16}O_x + 45\%$ Alundum using the catalytically active oxide powder as prepared in Example 15 and the inert support material described in Example 1. These catalysts were prepared as follows. For each of the following examples, 25 grams of the catalytically active oxide powder described in Example 15 was ball milled with 300 ml distilled water for about 16 hours. This material was dried at 110° C. for about 60 hours. This material was further ground to pass 100 mesh (0.149 mm) screen.

12.3 of Norton Alundum SA 5209, described above, was ground and screened to pass 10/20 mesh (2.00 mm/0.841 mm), in order to be suitable for use in 20 cc reactors. About 2 grams of distilled water was sprayed onto the support material, having been charged to a rolling glass jar, and the mixture was rolled for 2 minutes. 15 grams active powder was then charged to the rolling jar in 5 equal increments, with rolling times of one-half to about 3 min. between each addition. After the fourth increment was added and rolled, 1.0 gram distilled water was sprayed on the coated support and these were rolled for 2 min. After the final increment was added, the mixture was rolled for 6 min. and was thereafter dried at 110° C. for about 16 hrs. The catalysts were then calculated with heating from 200° C. to 400° C. at a rate of 5° C. per minute with heating at 400° C. for 1 hour.

Example 20

A catalyst having the formula 55% $V_{1.0}P_{1.16}O_x + 45\%$ Alundum was prepared as described in Examples 16-19, with the exception that the catalytically active oxide material was ball milled in isobutanol rather than in water before the initial drying and coating steps.

The catalysts described in Examples 15-20 were used to produce maleic anhydride from butane using a 20 cc fixed-bed reactor consisting of a length of stainless steel tubing having an outer diameter of about 1.3 cm. and having a full length 0.31 cm. axial thermowell. The reactor was heated with a split stainless steel block furnace. Recovery of product and analysis of tail gases were accomplished as described above. The reaction conditions and results of the tests run are described in Table II.

As is demonstrated in Table II, catalysts consisting of an inert support and a catalytically active oxide material consisting essentially of the mixed oxides of vanadium and phosphorus, wherein the catalytically active oxide material is present in a coating of the inert support in an amount greater than 50 wt.% based upon the combined weight of the support and catalytically active material provide yields and selectivity of butane to maleic anhydride greater than those yields obtained when the catalytically active oxide material is present in a pelleted (100%) form.

Thus it should be apparent to those skilled in the art that the subject invention accomplishes the objects set forth above. It is to be understood that the subject invention is not to be limited by the examples set forth herein. These have been provided merely to demonstrate operability, and the selection of specific catalytically active oxide materials, support material, hydrocarbon feedstocks and reaction conditions can be determined from the total specification disclosure provided without departing from the spirit of the invention herein disclosed and described, the scope of the invention being limited solely by the scope of the attached claims.

Thus it should be apparent to those skilled in the art that the subject invention accomplishes the objects set forth above. It is to be understood that the subject invention is not to be limited by the examples set forth herein. These have been provided merely to demonstrate operability, and the selection of specific catalytically active oxide materials, support material, hydrocarbon feedstocks and reaction conditions can be determined from the total specification disclosure provided without departing from the spirit of the invention herein disclosed and described, the scope of the invention including modifications and variations that fall within the scope of the attached claims.

TABLE I

| | Butane Feed Over $V_{1.0}P_{1.2}U_{0.2}O_x$ Catalyst on Alundum SA 5209 Support | | | | | | | |
|---|---|---|---|---|---|---|---|---|
| | | Temp. (°C.) | | Air/HC | Contact | Maleic Anhydride | | Hours on |
| Example No. | Weight % Active | Bath | Reactor | Ratio | Time (Sec.) | % Yield | % Selectivity | Stream |
| 1 | 30 | 400 | 408 | 60/1 | 1.0 | 13.5 | 54.6 | 21.6 |
| 2 | 50 | 420 | 442 | 70/1 | 1.0 | 43.0 | 57.9 | 118.0 |
| 3 | 50 | 420 | 438 | 60/1 | 2.0 | 54.2 | 60.1 | 142.1 |
| 4 | 70 | 430 | 449 | 74/1 | 2.0 | 59.9 | 65.3 | 144.7 |
| 5 | 70 | 430 | 449 | 74/1 | 2.0 | 61.3 | 67.9 | 161.6 |
| 6 | 55 | 420 | 433 | 60/1 | 2.0 | 59.4 | 66.1 | 239.9 |
| 7 | 55 | 425 | 439 | 60/1 | 2.0 | 59.0 | 63.9 | 242.6 |
| 8 | 55 | 425 | 441 | 60/1 | 2.0 | 62.5 | 66.5 | 246.7 |
| 9* | (100 pelleted) | 410 | 439 | 70/1 | 1.0 | 47.0 | 52.4 | 66.5 |
| 10* | 100 (pelleted) | 380 | 401 | 60/1 | 2.1 | 56.4 | 63.3 | 92.0 |
| 11* | 100 (tabletted) | 390 | 413 | 60/1 | 2.1 | 54.3 | 57.9 | 96.7 |
| 12* | 100 (tabletted) | 380 | 399 | 60/1 | 2.0 | 59.2 | 64.3 | 140.8 |
| 13* | 100 (tabletted) | 380 | 401 | 60/1 | 2.0 | 56.8 | 60.2 | 121.7 |
| 14* | 100 (tabletted) | 410 | 443 | 70/1 | 1.0 | 44.7 | 48.8 | 117.3 |

*No support used in Examples 9–14.

TABLE II

| | Butane Feed Over $V_{1.0}P_{1.16}O_x$ Catalyst on Alundum SA 5209 Support | | | | | | | |
|---|---|---|---|---|---|---|---|---|
| | | Temp. (°C.) | | | | Maleic Anhydride | | |
| Example No. | Weight % Active | Bath | React. | Air/HC Ratio | Contact Time | % Yield | % Selectivity | Hours On Stream |
| 15* | 100 (pelleted) | 440 | 456 | 58/1 | 2.0 | 43.5 | 49.1 | 140 |
| 16 | 55 | 430 | 445 | 66/1 | 1.07 | 53.7 | 58.4 | 41.2 |
| 17 | 55 | 410 | 418 | 62/1 | 2.17 | 61.1 | 61.1 | 45.5 |
| 18 | 55 | 405 | 410 | 61/1 | 2.20 | 54.4 | 63.6 | 64.2 |
| 19 | 55 | 410 | 416 | 62/1 | 2.19 | 55.9 | 62.3 | 69.5 |
| 20 | 55 | 435 | 442 | 68/1 | 2.08 | 53.0 | 57.4 | 118.7 |

*No support used in Example 15.

We claim:

1. A process for the production of maleic anhydride by the oxidation of n-butane, n-butenes, 1,3 butadiene or a mixture thereof with molecular oxygen or a molecular oxygen-containing gas in the vapor phase at a reaction temperature of 250° C. to 600° C. in the presence of a catalyst, wherein said catalyst comprises an essentially inert, at least partially porous support of at least about 20 microns in diameter, said support having an outer surface, and a catalytically active oxide material coating on said outer surface of said support which strongly adheres to said outer surface of said support wherein said oxide material consists essentially of the mixed oxides of vanadium and phosphorus, present in an amount greater than 50% to about 80% by weight of the combined support and oxide material wherein said oxide material is applied to said outer surface of said support by partially wetting said support with a liquid, contacting the partially wet support with a powder of said oxide material, and effecting said oxide coating.

2. A process for the production of maleic anhydride as described in claim 1, wherein n-butane is reacted.

3. A process for the production of maleic anhydride as described in claim 1 wherein said catalytically active oxide material is represented by the empirical formula $$V_1P_aO_x$$

wherein a = 0.1 to 10; and x is the number of oxygens required to satisfy the valence requirements of the other elements.

4. A process for the production of maleic anhydride as described in claim 1 wherein said support is selected from the group consisting of silica, alumina, alumina-silica, Alundum, silicon carbide, titania and zirconia.

5. A process for the production of maleic anhydride as described in claim 1 wherein said catalytically active oxide material is present in an amount from about 55% to about 70% by weight of the combined support and oxide material.

6. A process for the production of maleic anhydride as described in claim 1 wherein said catalytically active oxide material is present in an amount of about 55% by weight of the combined support and oxide material.

7. A process for the production of maleic anhydride as described in claim 1 wherein said catalytically active oxide material is present in an amount of about 70% by weight of the combined support and oxide material.

8. A process for the production of maleic anhydride as described in claim 1, wherein the catalytically active oxide material is represented by the formula $$V_1P_{1.16}O_x$$

wherein x is the number of atoms of oxygen required to satisfy the valence requirements of the other elements.

9. A process for the production of maleic anhydride by the oxidation of n-butane, n-butenes, 1,3 butadiene or a mixture thereof with molecular oxygen or a molecular oxygen-containing gas in the vapor phase at a reaction temperature of 250° C. to 600° C. in the presence of a catalyst, wherein said catalyst comprises an essentially inert, at least partially porous support of at least about 20 microns in diameter, said support having an outer surface, and a catalytically active oxide material coating on said outer surface of said support which strongly adheres to said outer surface of said support wherein said oxide material consists essentially of the mixed oxides of vanadium, phosphorus and uranium, present in an amount greater than 50% to about 80% by weight of the combined support and oxide material wherein said oxide material is applied to said outer surface of said support by partially wetting said support with a liquid, contacting the partially wet support with a powder of said oxide material, and effecting said oxide coating.

10. A process for the production of maleic anhydride as described in claim 9, wherein n-butane is reacted.

11. A process for the production of maleic anhydride as described in claim 9, wherein said catalytically active oxide material is represented by the empirical formula $$V_a P_b U_c O_x$$

wherein
- a and b are 0.1 to 10;
- c is 0.01 to 5; and
- x is the number of oxygens to satisfy the valence requirements of the other elements present.

12. A process for the production of maleic anhydride as described in claim 9 wherein said inert support is selected from the group consisting of silica, alumina, alumina-silica, Alundum, silicon carbide, titania and zirconia.

13. A process for the production of maleic anhydride as described in claim 9 wherein said catalytically active oxide material is present in an amount from about 55% to about 70% by weight of the combined support and oxide material.

14. A process for the production of maleic anhydride as described in claim 9 wherein said catalytically active oxide material is present in an amount of about 55% by weight of the combined support and oxide material.

15. A process for the production of maleic anhydride as described in claim 9 wherein said catalytically active oxide material is present in an amount of about 70% by weight of the combined support and oxide material.

16. A process for the production of maleic anhydride as described in claim 9 wherein said catalytically active oxide material is represented by the empirical formula $$V_a P_b U_c O_x$$

wherein
- a and b are 0.5 to 3;
- c is 0.1 to 0.5; and
- x is the number of oxygens required to satisfy the valence requirements of the other elements present.

17. A process for the production of maleic anhydride as described in claim 9 wherein said catalytically active oxide material is represented by the formula $V_1 P_{1.2} U_{0.2} O_x$.

* * * * *